(12) United States Patent
Martin et al.

(10) Patent No.: US 9,664,659 B2
(45) Date of Patent: May 30, 2017

(54) APPARATUS AND METHOD FOR TESTING GAS METERS

(71) Applicant: Dresser, Inc., Addison, TX (US)

(72) Inventors: Jeff Thomas Martin, Spring, TX (US); Andrew Logan Perkins, Houston, TX (US)

(73) Assignee: Dresser, Inc., Addison, TX (US)

( * ) Notice: Subject to any disclaimer, the term of this patent is extended or adjusted under 35 U.S.C. 154(b) by 225 days.

(21) Appl. No.: 14/534,025

(22) Filed: Nov. 5, 2014

(65) Prior Publication Data

US 2016/0123939 A1 May 5, 2016

(51) Int. Cl.
*G01F 25/00* (2006.01)
*G01N 33/00* (2006.01)

(52) U.S. Cl.
CPC ....... *G01N 33/0006* (2013.01); *G01F 25/003* (2013.01); *G01F 25/0053* (2013.01)

(58) Field of Classification Search
None
See application file for complete search history.

(56) References Cited

U.S. PATENT DOCUMENTS

| 4,658,634 | A | * | 4/1987 | Killough | G01F 25/003 |
| | | | | | 138/26 |
| 4,922,721 | A | * | 5/1990 | Robertson | F25B 21/02 |
| | | | | | 62/237 |
| 4,996,870 | A | | 3/1991 | Deutsch | |
| 5,455,781 | A | | 10/1995 | Reynal et al. | |
| 6,453,721 | B1 | | 9/2002 | Grzeslo et al. | |
| 6,640,140 | B1 | | 10/2003 | Lindner et al. | |
| 7,212,953 | B1 | | 5/2007 | Artiuch | |
| 7,860,677 | B2 | | 12/2010 | Artiuch | |
| 8,248,215 | B2 | | 8/2012 | Bibelhausen et al. | |
| 2003/0234044 | A1 | | 12/2003 | Shajii et al. | |
| 2009/0112368 | A1 | * | 4/2009 | Mann, III | B64F 1/364 |
| | | | | | 700/275 |

(Continued)

FOREIGN PATENT DOCUMENTS

EP 1785702 A2 5/2007

OTHER PUBLICATIONS

European Search Report and Written Opinion issued in connection with corresponding EP Application No. 15192968.4-1553 dated Apr. 15, 2016.

*Primary Examiner* — Robert R Raevis
(74) *Attorney, Agent, or Firm* — Paul Frank + Collins P.C.

(57) ABSTRACT

An apparatus that is configured to test operation of a gas meter. The apparatus can include a process control member with operative circuitry that provides all functionality necessary to execute the test and to analyze the resulting data. This functionality includes data processing functions and a web server to allow communication between the apparatus and a remote device via a network. In one embodiment, the operative circuitry includes a first circuitry to regulate operation of a fluid moving unit that provides fluid to a meter-under-test. The operative circuitry can also include a second circuitry to collect data from one or more sensors disposed on the meter-under-test. The operative circuitry can also have a third circuitry to perform various operations necessary to calculate, in one example, a value for an operative characteristic that relates to the accuracy of the meter-under-test.

9 Claims, 6 Drawing Sheets

(56) References Cited

U.S. PATENT DOCUMENTS

| | | | |
|---|---|---|---|
| 2011/0172524 A1* | 7/2011 | Hidem | A61M 5/14 600/431 |
| 2012/0019351 A1* | 1/2012 | Bougaev | G06F 11/3031 340/3.5 |
| 2013/0304411 A1 | 11/2013 | Berndt et al. | |
| 2014/0060449 A1* | 3/2014 | Dole | A01J 7/04 119/652 |

* cited by examiner

APPARATUS AND METHOD FOR TESTING GAS METERS

BACKGROUND

The subject matter disclosed herein relates to diagnostic testing and proving of gas meters, with particular discussion about an apparatus and a method for proving gas meters that embody features to administer the test or "proof," to process and to store data, and to convey results of the proof to a web-based user interface.

Techniques to test or prove gas meters can ensure the accuracy and performance of a meter-under-test. These techniques typically pass a test gas through the meter-under-test and through a second meter, or "master meter," that is known to meet some accepted performance standard. To arrive at the meter accuracy, or meter proof, the techniques look to the relationship between the volume of air that passes through the meter-under-test and the volume registered by the master meter.

In conventional configuration, the test systems to administer this proof have a bi-furcated structure. This structure includes a first part that embodies a cart-like component with the master meter(s), a fluid source (e.g., a blower), and a control interface. Notably, the structure also requires a second part, typically a computer that couples with the control interface via an appropriate connector (e.g., USB, RS-232, etc.). This computer executes software that is necessary to administer the proof (i.e., to regulate operation of the blowers), as well as to perform the data analysis to arrive at the meter proof.

BRIEF DESCRIPTION OF THE INVENTION

This disclosure introduces a test apparatus with a structure that is unique relative to these conventional test systems. This structure integrates a control member with features that forego the need for any separately enabled computer or computing device to instruct the apparatus to administer and to generate results of the test. In one aspect, this control member is configured to operate the fluid source as set out in the requisite test protocol. The control member is also configured to communicate with sensors disposed on the meter-under-test to collect and store data during the test. The control member can, in turn, process the collected data to generate diagnostic information locally on the test apparatus. As an added benefit, the test apparatus can integrate into a network system to allow for an end user to access the diagnostic information, and data generally, from a remote location, typically by way of web-based user interface.

BRIEF DESCRIPTION OF THE DRAWINGS

Reference is now made briefly to the accompanying drawings, in which.

Figure 1:
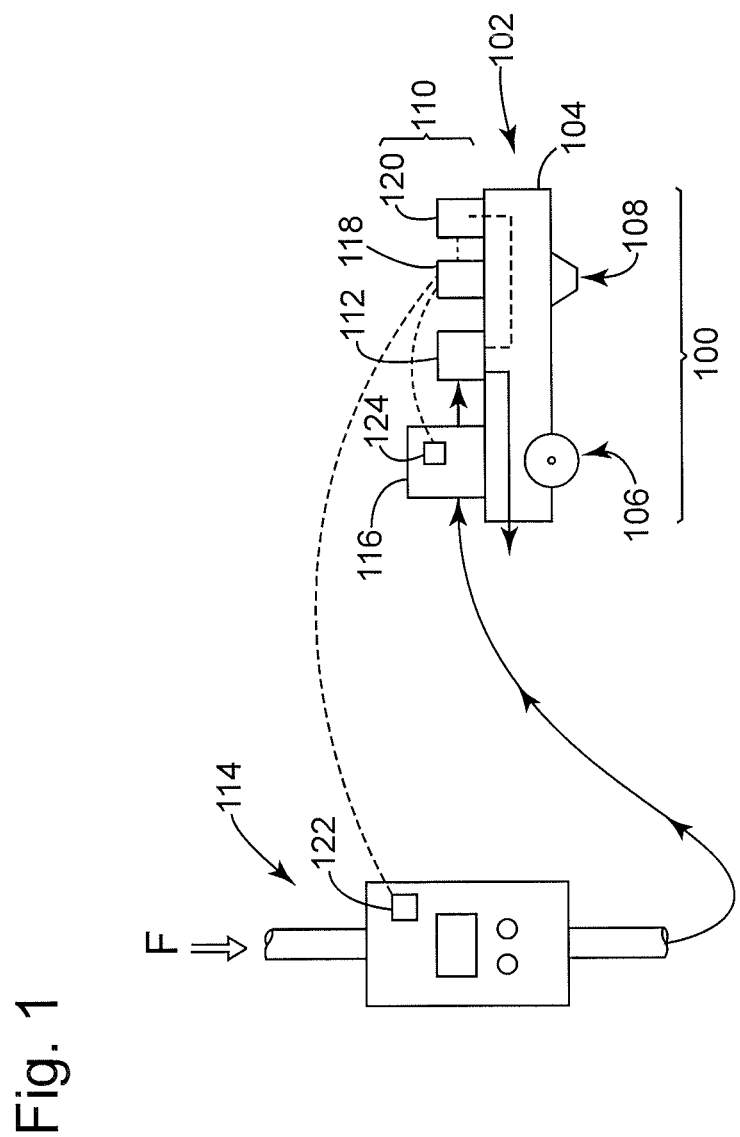
FIG. 1 depicts a schematic diagram of an exemplary embodiment of a test apparatus.

Where applicable like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

Existing systems for proving gas meters (and related devices) are generally simple in design. In conventional practice, these existing proving systems consist of a cart-like device (also "cart") that houses hardware (e.g., test meters, pump, sensors and sensor interface, etc.) to measure the accuracy of a target meter in the field. These systems also require a computer (typically a lap-top computer) with custom software that interfaces with the cart both to administer the "proof" and to process the data to quantify the results. It has been found, however, that the practice of using a relatively "dumb" cart with separate software makes these conventional systems particularly dependent on synergies between various software components (i.e., the custom software, the operating system found on the laptop computer, and any firmware and drivers found on the cart to talk with the computer). That is, updates in any one of these software components more often than not render the proving system inoperative until the necessary patches and/or updates percolate through to the other software components of the system.

The embodiments below offer a solution that works, in the broadest sense, independent of the software components necessary to prove the target meter. These embodiments integrate all of the components (e.g., hardware and software) necessary to perform, quantify, and transmit the results of the meter proof on-board a mobile platform that is conducive to easy transport. This solution at least eliminates use of the operating system. In turn, any component updates, for example to implement new functionality to the platform device, happen at the pleasure of the product owner/software developer, rather than at the behest of the operating system.

In addition to components to execute and quantify results, the components in the subject platform integrate web server software (also a "web server"). This feature, in particular, is not supported in the bi-furcated design of conventional practice. On the other hand, use of the web server on the present embodiments allow an end user to access all of the functionality of the platform from a remote location, often through a web-based user interface. The web server also configures the platform to serve up data and information to the end user through the web-based user interface. This feature, effectively, creates an autonomous testing platform that requires only a connection to power, air (or fluid), and a network (wired or wireless, as desired) to complete the proof of the target meter. Remote access functionality also allows control and access to multiple platforms in disparate locations to effectively aggregate testing and data collection functions from a single location.

FIG. 1 depicts a schematic diagram of an exemplary embodiment of a test apparatus 100. The test apparatus 100 includes a platform 102 that is configured to transit among locations (e.g., from a first position to a second position).

The platform 102 can have a base structure 104 and one or more support members (e.g., a first support member 106 and a second support member 108). The test apparatus 100 can also include a test rig 110 with, in one implementation, a fluid moving unit 112 that couples with and is configure to transfer a fluid F through a meter-under-test 114 (also, "target meter 114") and one or more master meters (e.g., a first master meter 116). These master meters can also integrate with the base structure 104. In one implementation, the fluid F can exhaust from the fluid moving device 112 into the base structure 104. The test rig 110 also has a diagnostic unit with a sensor member 118 that couples with a process control member 120. The sensor member 118 can couple with one or more sensors (e.g., a first sensor 122 and a second sensor 124), one each disposed on the target meter 114 and the first master meter 116. Examples of the sensors 122, 124 can include thermocouples, thermistors, transducers, and like devices that are sensitive to certain operating conditions on the meters 114, 116. These devices can generate analog and digital signals, wherein the sensor member 118 and/or the process control member 120 are appropriately configured to utilize the type of signals for purposes of the functions disclosed herein.

Broadly, the test apparatus 100 offers a unique solution that integrates data processing with mobility to improve on conventional systems that are used to characterize gas meters in the field. As noted above, conventional proving systems offer limited, if any, functions to process data, let alone to quantify the necessary characteristics of the meter-under-test 114 in combination with features to offer web-based services to provide ready access to data. These limitations require an end user (e.g., operator and/or technician) to utilize a separate computing device to render information that is useful to understand the operation of the meter-under-test.

The embodiments herein, in this regard, forgo this requirement, instead outfitting the test apparatus 100 in a manner that integrates processing capability (e.g., in the form of the diagnostic unit) along with the other components necessary to administer the requisite test protocols on the meter-under-test. These improvements, in turn, configure the test apparatus 100 to deliver the outcome of the test protocol in a format that is readily amenable for transmission over, for example, a network to a web-based portal and/or application (or "app") running on a device remote the test apparatus 100. In one embodiment, as noted above, the process control member 120 can have one or more executable instructions (e.g., software, firmware, etc.) that are configured to implement the web server that is configured to host one or more display pages for display on a user interface.

The platform 102 is configured to integrate the various members together. At a structural-level, this configuration can support the weight and disposition of each of the members, while at the same time offering mobility to ease the use of the test apparatus 100 by an end user to move, set-up, and administer the test protocol quickly and efficiently. Examples of the base structure 104 can have a frame that is constructed of materials, typically metals in a variety of forms, e.g., tubes, plates, etc. In one implementation, the frame can serve to dampen noise and vibration during operation of the test apparatus 100. This construction can accommodate fasteners (e.g., bolts, screws, etc.) that are useful to secure the members 112, 116, 118, 120 to the frame. The support members 106, 108 can serve both to facilitate mobility (e.g., as wheels and/or castors) and support (e.g., as stanchions, feet, etc.). In this way, the end user can position (e.g., roll) test apparatus 100 within proximity of the target meter 114 to perform the test protocol.

The process control member 120 can be outfit with hardware and executable instructions (e.g., software, firmware, etc.) that allow the test apparatus 100 to perform functions to execute the test protocol essentially autonomously. These functions, for example, regulate operation of the fluid moving unit 112, which is also a feature not found on conventional systems that test or "prove" operation of the target meter 114. Conventional systems, instead, require a separate "operative" device (that is typically a computer or like peripheral device) with software particularly configured to appropriately drive the fluid moving unit 112 to administer the test protocol. In other configurations, the functions process data to quantify the operative characteristics of the target meter 114. This feature also foregoes the need for the peripheral device in lieu of capabilities found on-board the test apparatus 100. Moreover, in one aspect, the process control member 120 can be configured to read, write, and/or store data to a repository (also "database"), which is also found on-board the test apparatus 100. This repository can retain records, historical information, and like data that may reflect implementation of the test protocol at various times, at various locations, and across a plurality of target meters (e.g., target meter 114). As compared to conventional systems, the repository offers a distinct advantage to allow the device to retain information, which effectively frees the end user to employ the test apparatus 100 to gather data and perform additional detailed analysis beneficial to the end user, operator, and/or end user of the target meter 114. In one example, the web server is configured to allow access to the repository via that user interface.

In one embodiment, the test apparatus 100 may include a display that is useful to show, or display, the user interface. Examples of the display include LCDs and like devices, which can couple with the process control member 120. These types of devices can reside locally on the test apparatus 100, where the display is configured for the user interface to display one or more display pages. Other configurations may rely on a separate, remote device to provide the display for use to show and display the display pages.

Figure 2:
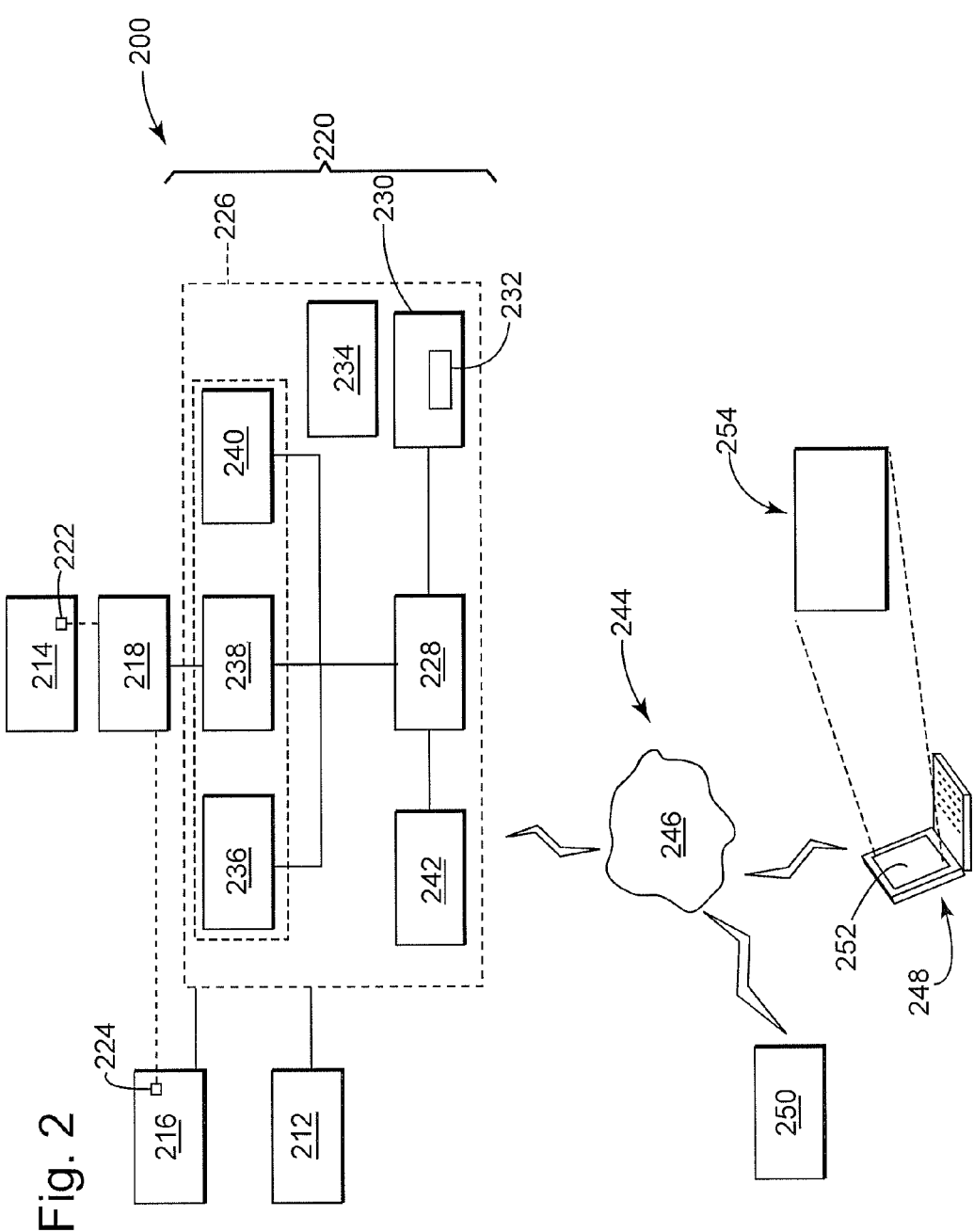
FIG. 2 depicts a schematic diagram of an exemplary embodiment of a test apparatus with details of the structure for a control member integrated therein.

FIG. 2 depicts a schematic diagram of an exemplary embodiment of a test apparatus 200 that can help visualize these improvements. The process control member 220 can include an operative circuit 226 with a processor member 228 that couples with a memory member 230 having one or more executable instructions 232 stored thereon. The operative circuit 226 can also include a repository 234, which may embody a separate device (as shown) or, in one example, embody all or part of the memory member 230. In addition, the operative circuit 226 can also include circuitry (e.g., a first circuitry 236, a second circuitry 238, and a third circuitry 240) and a communication device 242. Examples of the communication device 242 include antenna, transmitter/receivers, port connectors (e.g., USB, RS-232, Ethernet, etc.), and like devices that are useful to exchange data and signals between components over a network. As also shown in FIG. 2, the process control member 220 may communicate with a network system 244 via a network 246. Configurations for the network 246 can transfer data, information, and signals by way of wired protocols (e.g., Ethernet) and/or wireless protocols (e.g., Bluetooth®, wifi,). These protocols facilitate communication over the network 246 between the process control member 220, a terminal 248, and/or an external server 250. The terminal 248 may have a display 252 (or couple with the display 252) on which can be shown an interface 254.

Broadly, construction of the operative circuit 226 allows the test apparatus 200 to operate substantially autonomously to evaluate and report on the performance of the target meter 214. From an architecture-level, the processor 228 (and, also, the memory 230 and the executable instruction 232) can be configured to provide general, high-level control that facilitates the interactions among the circuitry 236, 238, 240. However, this disclosure does contemplate configurations in which one or more of the circuitry 236, 238, 240 can be configured with a processor member and/or a memory member, separate from the processor member 228 and the memory member 230.

In this connection, the circuitry 236, 238, 240 can afford the test apparatus 200 with unique features not found on systems of conventional architecture. The first circuitry 236 can include executable instructions (e.g., firmware and/or software) that configure the apparatus 100 for various operations. These executable instructions can configure the test apparatus 200 to exchange information with the network 248 via the communication device 242. This information may include instructions that originate from an end user, e.g., at the terminal 250, for purposes of creating and/or running the test protocols, accessing data, and like tasks. As noted herein, the executable instruction can also include (or enable) instructions to implement the web server that configures the test apparatus 200 to communicate with the network 246. The web server can be configured to host one or more display pages for display on the user interface. These display pages can present data on the user interface, notably, data that describes operation of the gas meter. Examples of the web server can implement any suitable protocol for this purpose, e.g., conventional TCP/IP protocol(s). In one implementation, the test apparatus 200 can be designated on the network 246 because the web server is configured to implement an Internet protocol (IP) address for the process control member 228. The terminal 248 may then access the test apparatus 200 using this IP address to allow access to the display pages by a remote device (e.g., terminal 248) over the network 246.

The second circuitry 238 can be configured to exchange information with the fluid moving unit 212. This information can include instructions that regulate operation of the fluid moving unit 212, often in accordance with the test protocol and/or higher-level instructions, e.g., received via the processor member 228. The third circuitry 240 can be configured to exchange information with the sensor member 220. This information may include data from sensors (e.g., the first sensor 222 and the second sensor 224) that is useful to quantify the operational characteristics of the target meter 214. Examples of the data can identify certain operating properties (e.g., temperature, volume, pressure, etc.) of the target meter 214 as well as other indicators that can be collected and analyzed to realize information about the performance of the target meter 214, as desired.

Figure 3:
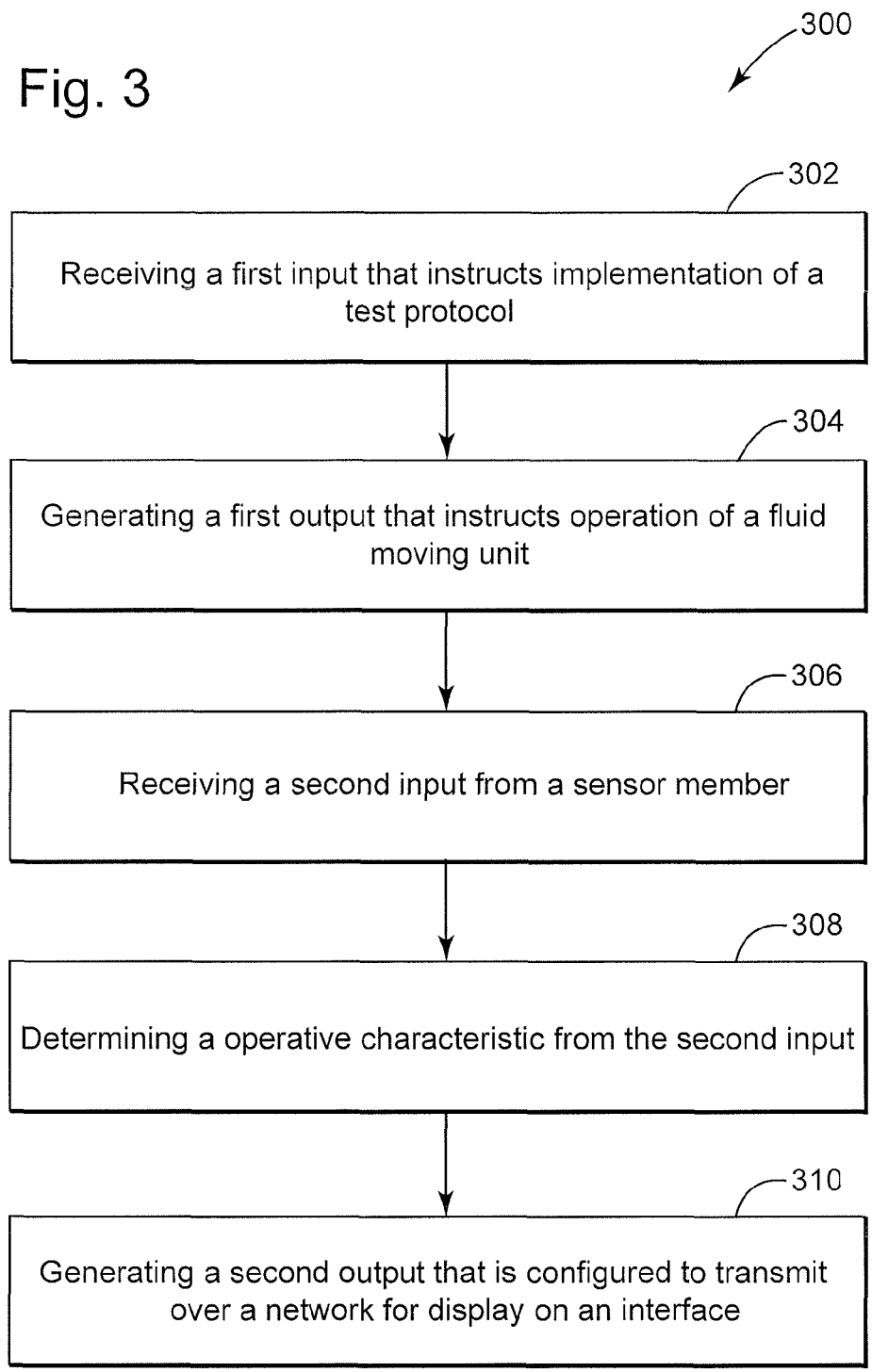
FIG. 3 depicts a flow diagram of an exemplary embodiment of a method for operating an example of a test apparatus for proving a meter-under-test.

FIG. 3 illustrates a flow diagram of an exemplary embodiment of a method 300 for characterizing a target meter. The method 300 includes, at step 302, receiving a first input that instructs implementation of a test protocol and, at step 304, generating a first output that instructs operation a fluid moving unit in accordance with the test protocol. The method 300 also include, at step 306, receiving a second input from the sensor member. This second input may identify data that relates to operation and/or operating parameters (e.g., temperature, flow, pressure, etc.) of the target meter 214 in response to the test protocol. The method 300 further includes, at step 308, determining an operative characteristic from the second input. In one embodiment, the method 300 can include, at step 310, generating a second output that is configured to transmit over a network for display on an interface. Examples of the second output may reflect the operative characteristic(s) of the target meter.

Referring also to FIGS. 2 and 3, the step of receiving the first input (e.g., at step 302) can leverage the architecture of the operative circuit 226 that allows for remote operation of the test apparatus 200. The first input may comprise signals with (and/or identifying) data that is associated with a desired operation for the test apparatus 200. In one illustrative embodiment, this data may identify a test protocol, which the operative circuit 226 can translate into instructions (of some useful format) to stimulate operation of the fluid moving unit 212. The signals may originate from on-board the test apparatus 200 by way of an input device (e.g., integrated buttons, touch screen, etc.). In other implementations, the signals may originate remote from the test apparatus 200. These types of remote signals may, for example, arise from interaction of the end user with the terminal 248 and/or interface 254, as contemplated herein.

The step of generating a first output (e.g., at step 304) introduces (and, also, regulates) fluid to the target meter 214. This step may include one or more steps for regulating operation of the fluid moving unit 212, e.g., by tuning the operation of the fluid moving unit 212 to achieve a specific target flow rate. As noted above, the first circuitry 236 can be configured to couple with the fluid moving unit 212. This arrangement dictates that the first output sets the operating parameters for the fluid moving unit 212. For example, the first input can identify an operating speed for the fluid moving unit 212 to pressurize and de-pressurize the fluid that enters the target meter 214 and the first master meter 216.

The step of receiving the second input (e.g., at step 306) can collect data about operation of the target meter 214. This step may include one or more steps for the method 300 to effectively provide a feedback loop to monitor performance of the target meter 214 in real-time. The steps may, for example, include one or more steps for starting data collection in response to input data or input signal (e.g., change from low to high voltage) and, in turn, one or more steps for stopping data collection after a certain pre-determined period of time and/or after changes in the input data or the input signal (e.g., change from high to low voltage) that indicates that the test protocol is complete. In one embodiment, the steps can include one or more steps for triggering data processing, as noted in connection with step 308 below.

At a hardware level, the second circuitry 238 may be configured with any variety of interfaces to exchange data with the sensor(s) 222, 224, either directly or via the sensor member 218. The second circuitry 238 may be configured to store and/or read the data from the sensor(s) 222, 224 to the repository 234. As noted above, this feature can retain historical records of performance of the target meter 214, for example, for the end user to access from the remote terminal configuration discussed in connection with FIG. 4 above. In one example, the method 300 may include one or more steps for writing data from the sensors 222, 224 to the repository 234.

The repository 234 may reside locally as integrated into the operative circuit 226, e.g., as shown in FIG. 2, or, in some configuration, the operative circuit 226 may be configured to exchange data over the network 246 to store the data on the external server 250 or some other remote (and/or "cloud-base") resource. In one implementation, the arrangement of the test apparatus 200 as part of the network system 244 can utilize file transfer protocol (FTP) format(s) to exchange the data between, e.g., the repository 234 and the terminal 248 and/or external server 250.

The step of determining the operative characteristic (e.g., at step 308) is useful to facilitate the integrated solution of the test apparatus 200. Examples of the operative characteristic can quantify the accuracy, repeatability, and other statistical information that can help qualify the operation the target meter 214. The third circuitry 240 may be configured to operate in a manner that arrives at values for one or more of these characteristics. This step may include one or more steps for comparing the data from the sensor(s) 222, 224 to a threshold value that identifies, for example, an expected volume that the target meter 214 is to achieve during the test protocol. This expected volume may reflect the volume measured at the first master meter 216. In other examples, the steps may include one or more steps for collecting data from the first master meter 216. The collected data can form the basis for the threshold value. In connection with the discussion above, the values for the operative characteristics can be stored in the repository 234, as desired.

The step of generating the second output (e.g., at step 310) can include steps to formulate the data for use with the interface 254. Broadly, the second output can indicate the relationship between the operative characteristic and the threshold value. These steps may include steps for formatting and/or arranging the data to transmit across the network 246. Such formatting may also coincide with operation of the web server to provide, or "serve-up," the data on one or more display pages for use with the interface 254. In one example, the method 300 can include steps to format the second output for use with a display that is located on-board the test apparatus 200. In another example, the method 300 can include one or more steps to format the second output for use with the interface 254. In both cases, the method 300 leverages the web server functionality to deliver the data, e.g., to the on-board display (discussed above) and/or the interface 254.

At the terminal 248, the interface 254 may be configured with icons, inputs, visual indicators, and like operative features that present on the display 252. These operative features can create a visual environment that allows the end user to understand the operation of the target meter 214. In some configurations, the operative features may allow the end user to access and view data about other meters (either alone, or in combination with the target meter 214), as dictated by the historical data found on the repository 234. In one aspect, the operative features can allow the end user to interact with the operative circuit 226 to modify the existing test protocols, develop new test protocols, and the like.

Figure 4:
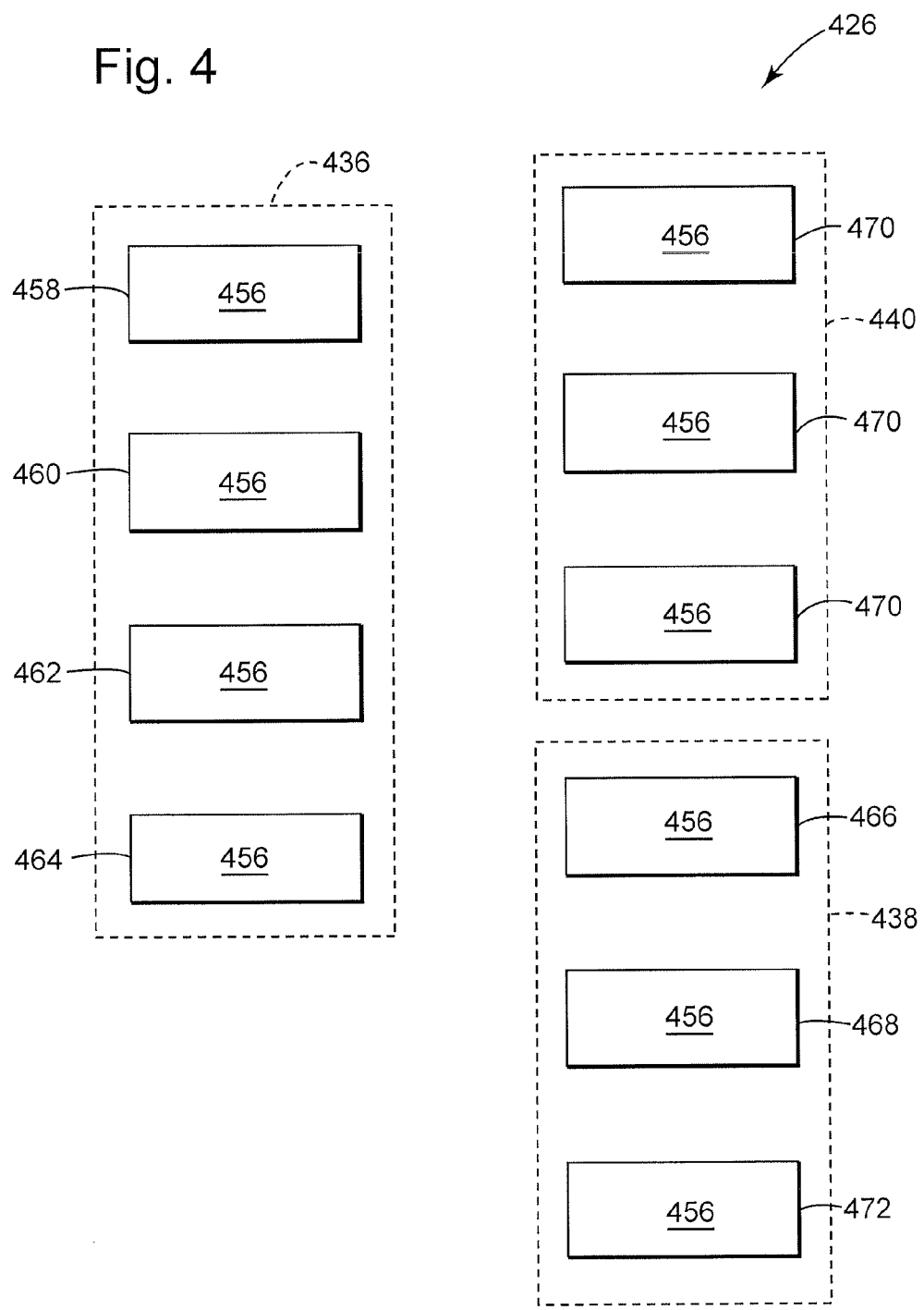
FIG. 4 depicts a schematic diagram of an exemplary embodiment of a test apparatus.

FIG. 4 illustrates a schematic diagram that represents an example of an operative circuit 426. At a relatively high level, this example can include one or more structural elements, identified generally by the numeral 456. Examples of the structural elements 456 can embody functions of the operative circuit 426, by way of the configuration of hardware, computer programs (e.g., software and firmware), and/or the combinations thereof. In this example, the first circuitry 436 is configured with a configuration element 458, a database element 460, a file transfer element 462, a data processing element 464. The second circuitry 438 is configured with a flow control element 466, a motor control element 468, and a communication element 472. In one example, the third circuitry 440 is configured with one or more sensor elements 470, one each configured for use with a corresponding sensor (e.g., first sensor 124 of FIG. 1). In one implementation, the first circuitry 436 can also include a web server element, which can be configured for access to the database element 460 and/or other data repository, as desired.

The elements that make up each of the circuitry 436, 438, 440 can embody devices and instructions that enable the corresponding functionality that is integrated into the embodiments contemplated herein. The elements in the second circuitry 438, for example, can be configured to regulate operation of the fluid moving unit 212 (FIG. 2). The flow control element 466 can monitor the flow to the target meter 214 (FIG. 2) and the master meter 216 (FIG. 3). This element may, in turn, regulate operation of the motor control element 468 to modulate the operative signal that drives the fluid moving unit 212 (FIG. 2). The communication element 470 can operate to exchange the operative signal, e.g., with the fluid moving unit 212. Examples of the communication element 470 may embody USB connectors, as well as wireless connective device as desired. This element may incorporate an analog-to-digital converter, or like conversion device, to properly situate the incoming signals and the outgoing signals for use at the respective device. At the third circuitry 440, the sensor elements 472 can also exchange signals with the sensors, whether being configured with the appropriate communication device or via the communication element 470.

In the first circuitry 436, the configurations of elements are directed, generally, to process, access, and exchange data. The configuration element 458 can allow the end user to modify the test protocols by, for example, offering a selection of various process variables (e.g., speed, flow, etc.) and/or a coding environment to modify the steps/instructions of the test protocol. Examples of the database element 460 can facilitate storage of the data, for example, on the repository 234 (FIG. 2). The file transfer element 462 can host data and/or make data available for transfer using one or more transfer protocols, e.g., file transfer protocol (FTP). The data processing element 464 is useful to execute processes on data to quantify the operative characteristics of the target meter 214.

Figure 5:
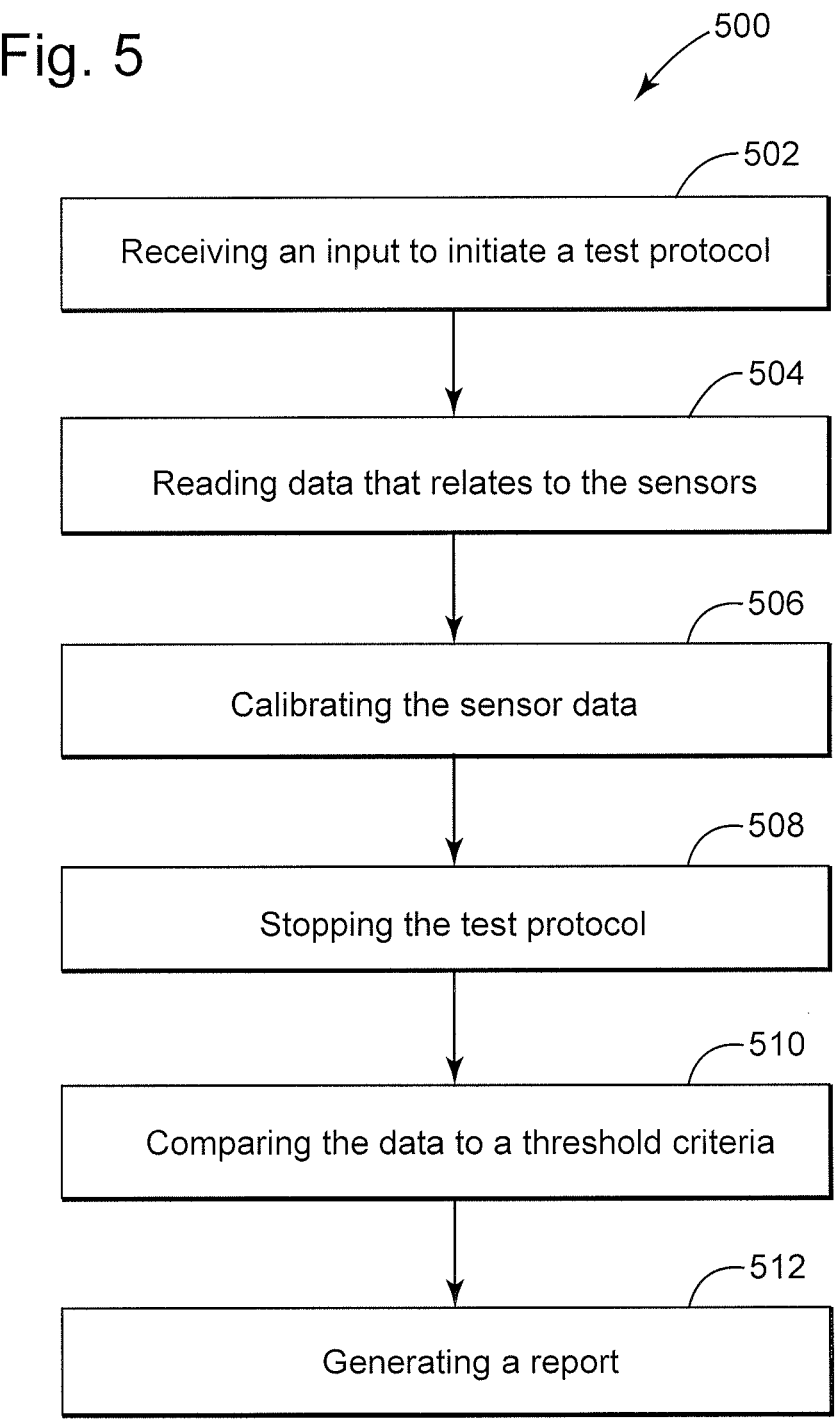
FIG. 5 depicts a flow diagram of an exemplary embodiment of a method for administering a test protocol on an example of a test apparatus.

FIG. 5 depicts a flow diagram of a method 500 for executing a test protocol and processing data for use on and/or embodied by the data processing element 464 (FIG. 4). The method 500 can include, at step 502, receiving an input that indicates that a test protocol should be initiated and, at step 504, reading data that relates to the sensors. The method 500 also includes, at step 506, applying a sensor offset to the values, at step 508, stopping the test protocol, and, at step 510, comparing the data to a threshold criteria. In one embodiment, the method 500 can include, at step 512, generating a report that reflects the relative position of the data with respect to the threshold criteria. Examples of this report may, in turn, be transferred and/or exchanged in a manner that displays on the interface 254 (FIG. 2) for use by the end user at the terminal 248 (FIG. 2).

Figure 6:
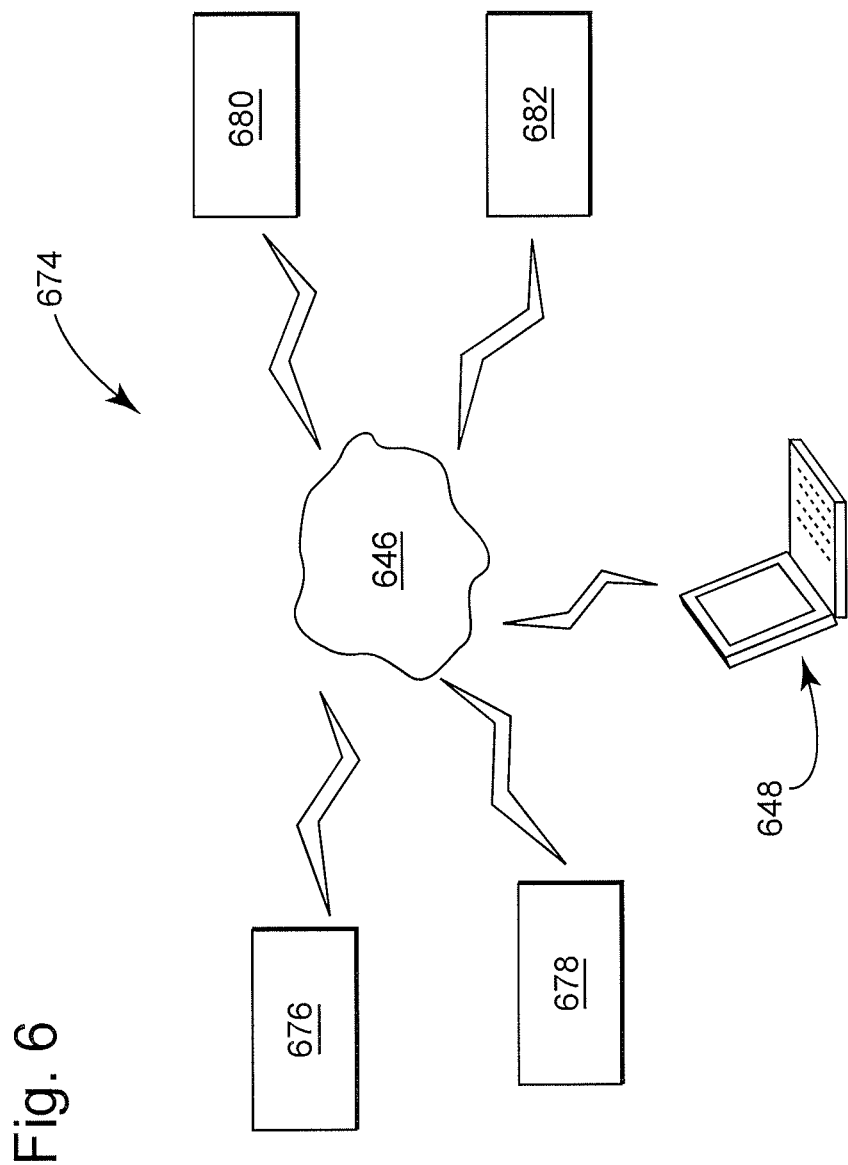
FIG. 6 depicts an example of a system that permits remote access to one or more test apparatus, each being configured in accordance with the discussion herein.

FIG. 6 illustrates an example of a test system 674 that takes advantage of the integrated features of the embodiments discussed above. In FIG. 4, the test system 674 includes a plurality of test apparatus (e.g., a first test apparatus 676, a second test apparatus 678, a third test apparatus 680, and a fourth apparatus 682). Each of the apparatus 676, 678, 680, 682 couple with the terminal 648 via the network 646. In one example, an end user at the terminal 648 can communicate with one or more the apparatus 676, 678, 680, 682. This access may utilize a web-based interface, e.g., a web portal and suitable IP address arrangement that allows for remote access to the requisite one of the apparatus 676, 678, 680, 682. This web-based interface may solicit information from the end user that indicates, for example, the selection of a specific test protocol. In other examples, the web-based interface may allow the end user to modify, upload, download, and/or otherwise access information on the test apparatus 676, 678, 680, 682. This feature can allow the end user to change certain parameters of test protocol, assign new test parameters to existing and/or new test protocols, and like operations that would, in conventional devices, require the end user to be located in close proximity to the target meter, e.g., for use of a USB and/or RS-232 cable and/or Bluetooth® communication.

In light of the foregoing, the embodiments described herein are configured to integrate additional functionality not found on conventional testing systems. These embodiments integrate, in one aspect, operative circuits that are configured to operate a fluid moving device and to provide a web server to allow for remote access of the device by way of a web-based user interface. A technical effect of such integration is to provide a test apparatus that operates substantially autonomously to execute a test protocol without the need for, or instruction by, a separately enabled computer with particularly formulated software.

One or more of the steps of the methods (e.g., method xxx) can be coded as one or more executable instructions (e.g., hardware, firmware, software, software programs, etc.). These executable instructions can be part of a computer-implemented method and/or program, which can be executed by a processor and/or processing device. The processor may be configured to execute these executable instructions, as well as to process inputs and to generate outputs, as set forth herein. For example, the software can run and/or reside on the device and/or as software, application, or other aggregation of executable instructions on a separate computer, tablet, lap top, smart phone, and like computing device.

The computing components (e.g., memory and processor) can embody hardware that incorporates with other hardware (e.g., circuitry) to form a unitary and/or monolithic unit devised to execute computer programs and/or executable instructions (e.g., in the form of firmware and software). Exemplary circuits of this type include discrete elements such as resistors, transistors, diodes, switches, and capacitors. Examples of a processor include microprocessors and other logic devices such as field programmable gate arrays ("FPGAs") and application specific integrated circuits ("ASICs"). Memory includes volatile and non-volatile memory and can store executable instructions in the form of and/or including software (or firmware) instructions and configuration settings. Although all of the discrete elements, circuits, and devices function individually in a manner that is generally understood by those artisans that have ordinary skill in the electrical arts, it is their combination and integration into functional electrical groups and circuits that generally provide for the concepts that are disclosed and described herein.

Aspects of the present disclosure may be embodied as a system, method, or computer program product. The embodiments may take the form of an entirely hardware embodiment, an entirely software embodiment (including firmware, software, etc.) or an embodiment combining software and hardware aspects that may all generally be referred to herein as a "circuit," "module" or "system." The computer program product may be embodied in one or more non-transitory computer readable medium(s) having computer readable program code embodied thereon.

Computer program code for carrying out operations for aspects of the present invention may be written in any combination of one or more programming languages, including an object oriented programming language and conventional procedural programming languages. Program code embodied on a computer readable medium may be transmitted using any appropriate medium, including but not limited to wireless, wireline, optical fiber cable, RF, etc., or any suitable combination of the foregoing.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for testing a target meter, said apparatus comprising:
   a platform configured to transit from a first position to a second position;
   a fluid moving unit disposed on the platform;
   a process control member disposed on the platform and configured to communicate with the fluid moving unit, the process control member having an operative circuit comprising a processor member and a memory member with executable instructions stored thereon; and
   a sensor member coupled with the operative circuit, the sensor member configured to communicate with one or more sensors,
   wherein the executable instructions comprise instructions that configure the process member for,
      receiving a first input that instructs the process control member to implement a test protocol;
      generating a first output that instructs operation of the fluid moving unit in accordance with the test protocol;
      receiving a second input from the sensor member with information that relates to operation of the target meter in response to the test protocol;
      using the second input, determining an operative characteristic for the target meter; and
      generating a second output that is configured to transmit over a network for display on a user interface, the second output reflecting the operative characteristic.

2. The apparatus of claim 1, wherein the operative circuit comprises a first circuitry that is configured to couple with the fluid moving unit, and wherein the first circuitry is configured to generate the first output to set an operating parameter of the fluid moving device.

3. The apparatus of claim 2, wherein the operative circuit comprises a second circuitry that is configured to exchange data with the one or more sensors via the sensor member.

4. The apparatus of claim 3, wherein the operative circuit comprises a third circuitry that is configured to process data from the second input to arrive a value for one or more operative characteristics of the target meter.

5. The apparatus of claim 1, wherein the executable instructions comprise instructions that configure the process member for,
    implementing a web server that is configured to host one or more display pages for display on the user interface.

6. The apparatus of claim 5, further comprising a communication device that is configured to exchange data including the second output over a network,
    wherein the executable instructions comprise instructions that configure the process member for,
    configuring the web server to implement an IP address for the process control member that allows access to the one or more display pages by a remote device over the network.

7. The apparatus of claim 5, further comprising a display coupled with the process control member and disposed locally on said apparatus, wherein the display is configured for the user interface to display the one or more display pages.

8. The apparatus of claim 1, wherein the executable instructions comprise instructions for,
    writing data from the one or more sensors to a repository.

9. The apparatus of claim 8, wherein the repository is integrated into the operative circuit.

* * * * *